(12) United States Patent
Spohn et al.

(10) Patent No.: US 8,403,909 B2
(45) Date of Patent: Mar. 26, 2013

(54) METHODS FOR CAPACITANCE VOLUME CORRECTION IN FLUID DELIVERY SYSTEMS

(75) Inventors: Michael A. Spohn, Butler, PA (US); Thomas P. Joyce, Wilkins Township, PA (US)

(73) Assignee: Medrad, Inc., Indianola, PA (US)

( * ) Notice: Subject to any disclaimer, the term of this patent is extended or adjusted under 35 U.S.C. 154(b) by 304 days.

(21) Appl. No.: 12/682,813

(22) PCT Filed: Oct. 8, 2008

(86) PCT No.: PCT/US2008/079160
§ 371 (c)(1),
(2), (4) Date: Apr. 13, 2010

(87) PCT Pub. No.: WO2009/051995
PCT Pub. Date: Apr. 23, 2009

(65) Prior Publication Data
US 2010/0222768 A1    Sep. 2, 2010

Related U.S. Application Data

(60) Provisional application No. 60/981,128, filed on Oct. 19, 2007.

(51) Int. Cl.
*A61M 31/00* (2006.01)
(52) U.S. Cl. ............... 604/506; 604/30; 604/247
(58) Field of Classification Search .......... 604/533, 604/251, 30–32, 35, 247, 249, 506
See application file for complete search history.

(56) References Cited

U.S. PATENT DOCUMENTS

| | | |
|---|---|---|
| 5,460,609 A | 10/1995 | O'Donnell |
| 5,573,515 A | 11/1996 | Wilson et al. |
| 5,800,397 A | 9/1998 | Wilson et al. |
| 5,873,861 A | 2/1999 | Hitchins et al. |
| 5,947,935 A | 9/1999 | Rhinehart et al. |
| 7,563,249 B2 | 7/2009 | Schriver et al. |
| 7,688,057 B2 | 3/2010 | Foss et al. |
| 2004/0254533 A1 | 12/2004 | Schriver et al. |
| 2005/0171487 A1 | 8/2005 | Haury et al. |

(Continued)

OTHER PUBLICATIONS

International Search Report and Written Opinion for counterpart International Patent Application No. PCT/US2008/079160 mailed on Dec. 4, 2008.

(Continued)

*Primary Examiner* — Laura Bouchelle
(74) *Attorney, Agent, or Firm* — James R. Stevenson; Christian E. Schuster; Gregory L. Bradley

(57) ABSTRACT

Methods for capacitance volume correction in fluid-containing expandable bodies and associated fluid pathways are disclosed. The methods may be applied in fluid delivery systems used to supply fluids to patients during radiographic imaging procedures, including angiography. The methods control delivery of fluid to a downstream process, including providing a fluid-delivery expandable body and a pressurizing element in fluid communication with the downstream process, pressurizing the expandable body by moving the pressurizing element in the expandable body to reduce volume therein, determining an over-travel distance for the pressurizing element, and ceasing movement of the pressurizing element after allowing the pressurizing element to over-travel the over-travel distance to compensate for expansion of the expandable body under pressure. The expandable body may be a syringe and the pressurizing element may be a plunger disposed within the syringe. Movement of the pressurizing element may be controlled by an algorithm associated with a computer.

20 Claims, 14 Drawing Sheets

U.S. PATENT DOCUMENTS

2005/0234407 A1   10/2005   Spohn et al.
2005/0234428 A1*  10/2005   Spohn et al. .................. 604/533
2006/0079843 A1    4/2006   Brooks et al.
2007/0129705 A1    6/2007   Trombley, III et al.
2007/0161970 A1    7/2007   Spohn et al.
2008/0086087 A1    4/2008   Spohn et al.

OTHER PUBLICATIONS

International Preliminary Report on Patentability and Written Opinion for counterpart International Patent Application No. PCT/US2008/079160 issued on Apr. 20, 2010.

* cited by examiner

METHODS FOR CAPACITANCE VOLUME CORRECTION IN FLUID DELIVERY SYSTEMS

CROSS REFERENCE TO RELATED APPLICATION

This application is a 371 national phase application of PCT International Application No. PCT/US08/79160, filed on Oct. 8, 2008, and designating the United States of America, which claims the benefit of U.S. Provisional Application Ser. No. 60/981,128, filed on Oct. 19, 2007, the contents of which are incorporated herein by reference.

BACKGROUND OF THE INVENTION

1. Field of the Invention

The embodiments of the invention disclosed herein relate generally to the field of diagnostic and therapeutic medical procedures involving the intravenous infusion of fluids such as contrast-enhanced radiographic imaging as an example and, further, to fluid delivery systems employing techniques to correct for capacitance volume effects in fluid-delivery bodies used in fluid delivery systems.

2. Description of Related Art

In many medical diagnostic and therapeutic procedures, a medical practitioner, such as a physician, injects a patient with a fluid. In recent years, a number of injector-actuated syringes and powered injectors for pressurized injection of fluids, such as contrast media (often referred to simply as "contrast"), have been developed for use in procedures such as angiography, computed tomography, ultrasound, and NMR/MRI. In general, these powered injectors are designed to deliver a preset amount of contrast at a preset flow rate.

Angiography is an example of a radiographic imaging procedure wherein a powered injector may be used. Angiography is used in the detection and treatment of abnormalities or restrictions in blood vessels. In an angiographic procedure, a radiographic image of a vascular structure is obtained through the use of a radiographic contrast medium which is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical contrast-enhanced radiographic imaging procedure such as angiography, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again such as stopcocks. The operator of the manual system controls the syringe and each of the valves to draw saline or contrast into the syringe and to inject the contrast or saline into the patient through the catheter connection.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector, except to start or stop the injection. A change in flow rate in such systems occurs by stopping the machine and resetting the injection parameters. Automation of contrast-enhanced imaging procedures using powered injectors is discussed, for example, in U.S. Pat. Nos. 5,460,609 to O'Donnell and 5,573,515 and 5,800,397 both to Wilson et al.

U.S. Pat. No. 5,800,397, for example, discloses an angiographic injector system having both high pressure and low pressure systems. The high pressure system includes a motor-driven syringe injector pump to deliver radiographic contrast material under high pressure to a catheter. The low pressure system includes, among other things, a pressure transducer to measure blood pressure and a pump to deliver a saline solution to the patient as well as to aspirate waste fluid. A manifold is connected to the syringe pump, the low pressure system, and the patient catheter. A flow valve associated with the manifold is normally maintained in a first state connecting the low pressure system to the catheter through the manifold, and disconnecting the high pressure system from the catheter and the low pressure system. When pressure from the syringe pump reaches a predetermined and set level, the valve switches to a second state connecting the high pressure system/syringe pump to the catheter, while disconnecting the low pressure system from the catheter and from the high pressure system. In this manner, the pressure transducer is protected from high pressures.

A feature disclosed in the Wilson et al. patents relate to synchronizing injection of radiographic contrast material with coronary blood flow and, thus, injecting the contrast material in pulses according to the cardiac cycle. However, it is known from this patent that inertial forces of moving contrast material and expansion of the containers and tubing associated with the system and used to conduct the contrast material to the patient via the catheter can cause a phase lag between movement of the syringe plunger within the injector syringe and movement of contrast material out of the catheter and into the patient. To adjust to the phase lag between syringe plunger movement and contrast injection into the patient, a variable time offset may be entered through a control panel such that the timing of the cardiac cycle can be offset by a selected time. Since the magnitude of the phase lag may be dependent on the frequency of heart rate, an algorithm within a computer associated with the control panel continuously and automatically adjusts the magnitude of the time offset based on the instantaneous heart rate during the injection of contrast material.

Another attempt to correct for "elasticity" errors introduced in a fluid delivery systems used to deliver contrast agent to a patient is known from United States Patent Application Publication No. 2006/0079843 to Brooks et al. This published application discloses a dual head injector that utilizes V-tubing in which the fluid paths for contrast agent and saline remain separate until substantially at the patient. By utilizing this type of V-tubing, the elasticity of the fluid delivery components (e.g., syringe, tubing, etc.) can be accommodated and there is reduced lag time in administration of a desired fluid to a patient. In a disclosed embodiment, two different fluid tubes are coupled via the V-tubing with a dual head injector and which are joined at one fluid entry point substantially at the patient. Thus, two fluid tubes merge together between the syringes of the dual head injector and the patient using the V-tubing.

The Brooks et al. publication further discloses that a Y-tubing arrangement has also been used to merge the flow paths of two syringes in a dual head injector, wherein the separate tubes merge relatively near the syringes so that a single fluid tube exists for the majority of the tubing. However, in this arrangement, the inherent elasticity of the syringes allows back flow from the "driven" syringe to the "non-driven" syringe during a pressure injection. Unless precautions are taken with such common tubing merging arrangements, the contents of the driven syringe may be pushed into the un-driven syringe and contaminate the contents of this syringe. One known solution to this backflow problem is to use check valves in the branch conduits of the Y-tubing fluid path. Additionally, Y-tubing introduces lag time between the supplying of the two different fluids. In particular, the entire contents of the Y-tubing shared portion must be flushed of one fluid before a second fluid can be delivered to the patient.

Moreover, it is known that in typical power injector systems there is inherent elasticity due to compression of the syringe plunger and the expansion of the syringe barrel. The shape and size of the syringe plunger affects the amount of elasticity present as well. The foregoing Brooks et al. publication discloses that the syringe plunger of the un-driven syringe in the dual head injector may be driven to a sufficient displacement to prevent the movement of fluid into the tubing associated with the un-driven syringe due to elasticity. The amount of displacement is a function of pressure present in the driven syringe and the type of syringes in use in the dual head injector. Closed-loop, open loop, and a combined open/closed loop approaches are disclosed in this publication for controlling the displacement movement of the syringe plunger in the un-driven syringe. A closed-loop approach to controlling displacement movement of the syringe plunger in the un-driven syringe entails measure of pressure and/or fluid flow in the driven syringe which is then used to perform closed-loop control of the injector ram associated with the un-driven syringe plunger to prevent back flow into the un-driven syringe due to elasticity. In an open-loop approach, measured values of typical elasticity and pressure in the driven syringe may be used to drive an appropriate displacement movement of the syringe plunger in the un-driven syringe. In a combined open/closed loop approach, the initial displacement applied to the un-driven syringe plunger upon initiation of an injection may be obtained from measured typical values, after which a closed-loop control may be initiated to maintain an equilibrated pressure between the driven and un-driven syringes and/or zero flow rate from the un-driven syringe.

In the foregoing contrast fluid delivery systems, indirect attempts are made to correct for "elasticity" errors that are known to occur when the systems are under pressure, but the proposed solutions are directed to specific/limited applications. The Wilson et al. patents disclose a simple time delay or variable time offset to adjust for a phase lag between syringe plunger movement and contrast injection into the patient, such that the timing of the cardiac cycle can be offset by a selected time. Brooks et al. address the limited problem of syringe plunger compression and syringe barrel expansion in a dual head injector system by operating the un-driven syringe thereof in a manner to prevent the back flow therein from the driven syringe. However, these approaches do not address capacitance or compliance volume errors in a comprehensive manner and, as a result, fail to address the under-delivery or over-delivery of contrast to the patient resulting from compliance or capacitance volume in the system "fluid path" components. As a result, less than optimal injection boluses may result and/or operation of the fluid delivery system can result in relatively large amounts of wasted contrast media.

SUMMARY OF THE INVENTION

Accordingly, a need generally exists for improved fluid delivery systems and methods for application in diagnostic and therapeutic medical procedures involving the intravenous infusion of fluids such as contrast-enhanced radiographic imaging that automatically corrects for systemic volume capacitance effects when the system is under pressure. Additionally, a need exists for a way to supply a sharp bolus of injection fluid to a patient while also delivering the full required or an accurate dosage of injection fluid to the patient. One solution that meets the foregoing needs relates to employing algorithm-based techniques to correct for capacitance volume effects in fluid-delivery bodies and other pathway components used in fluid delivery systems.

In medical procedures, it is often desirable to introduce a bolus, such as a unit dose of medication and/or diagnostic fluid, such as contrast media, intravenously by direct infusion to raise blood-level concentrations to a therapeutic and/or diagnostic level. It is often desirable to introduce a "sharp" bolus in which the medication and/or diagnostic fluid is introduced at increased pressure for rapid delivery into a specific location within the body. For example, a sharp bolus of contrast media may be defined as a distinct or defined column of liquid having well-defined opposing ends or boundaries. In one aspect, the method disclosed herein delivers a sharp bolus of medication and/or diagnostic fluid, delivers a full required or an accurate dosage of the medication and/or diagnostic fluid, and minimizes residual pressures in system components upon completion of the delivery of the sharp bolus.

In one embodiment, a method of capacitance volume correction is disclosed with respect to a fluid-containing and, typically at least partially, expandable or resiliently expandable body typically in fluid communication with a downstream process. The method includes pressuring the expandable body by reducing the volume in the expandable body with movement of a pressurizing element, and ceasing pressurization by stopping movement of the pressurizing element after allowing the pressurizing element to over-travel a sufficient distance to compensate for expansion of the expandable body under pressure. In one embodiment, the expandable body is a syringe and the pressurizing element is a plunger disposed within the syringe. Movement of the pressurizing element may be controlled by an algorithm associated with a computer device.

The method can also include abruptly isolating the expandable body from the downstream process after the pressurizing element over-travels a sufficient distance. The step of isolating the expandable body can include closing an isolation valve. In another aspect, the method can include the step of retracting the pressurizing element within the expandable body a sufficient distance to relieve pressure within the expandable body. In yet another aspect, the method can include opening the isolation valve to place the expandable body in fluid communication with a source of fluid for the expandable body. The expandable body can be refilled with fluid from the fluid source by retracting the pressurizing element within the expandable body.

In another embodiment, a method of capacitance volume correction in a syringe is provided. The syringe includes a plunger and is filled with an injection fluid. The method includes the steps of pressuring the syringe by reducing the volume in the syringe body with movement of the plunger, and stopping movement of the plunger after allowing the plunger to over-travel a sufficient distance to compensate for expansion of the syringe body under pressure.

The method can also include abruptly isolating the syringe from the downstream process after the pressurizing element over-travels a sufficient distance. The step of isolating the expandable body can include closing an isolation valve. In another aspect, the method can include the step of retracting the plunger within the syringe a sufficient distance to relieve pressure within the syringe body. In yet another aspect, the method can include opening the isolation valve to place the syringe in fluid communication with a source of injection fluid for the syringe. The syringe can be refilled by retracting the plunger within the syringe.

In another embodiment, a method of controlling delivery of fluid to a downstream process is provided and includes providing a fluid-containing expandable body in fluid communication with the downstream process. The expandable body can include a pressurizing element. The fluid-containing expandable body can be a syringe and the pressurizing element can be a plunger housed within the syringe. The method can include the steps of pressurizing the expandable body by moving the pressurizing element forward in the expandable body to reduce volume therein, and ceasing movement of the pressurizing element after allowing the pressurizing element to over-travel a sufficient distance to compensate for expansion of the expandable body under pressure.

The method can also include abruptly isolating the expandable body from the downstream process after the pressurizing element over-travels a sufficient distance. The step of isolating the expandable body can include closing an isolation valve. In another aspect, the method can include the step of retracting the pressurizing element within the expandable body a sufficient distance to relieve pressure within the expandable body. In yet another aspect, the method can include opening the isolation valve to place the expandable body in fluid communication with a source of fluid for the expandable body. The expandable body can be refilled with fluid from the fluid source by retracting the pressurizing element within the expandable body.

Further details and advantages will become clear upon reading the following detailed description in conjunction with the accompanying drawing figures, wherein like parts are identified with like reference numerals throughout.

DESCRIPTION OF THE PREFERRED EMBODIMENTS

Figure 1:
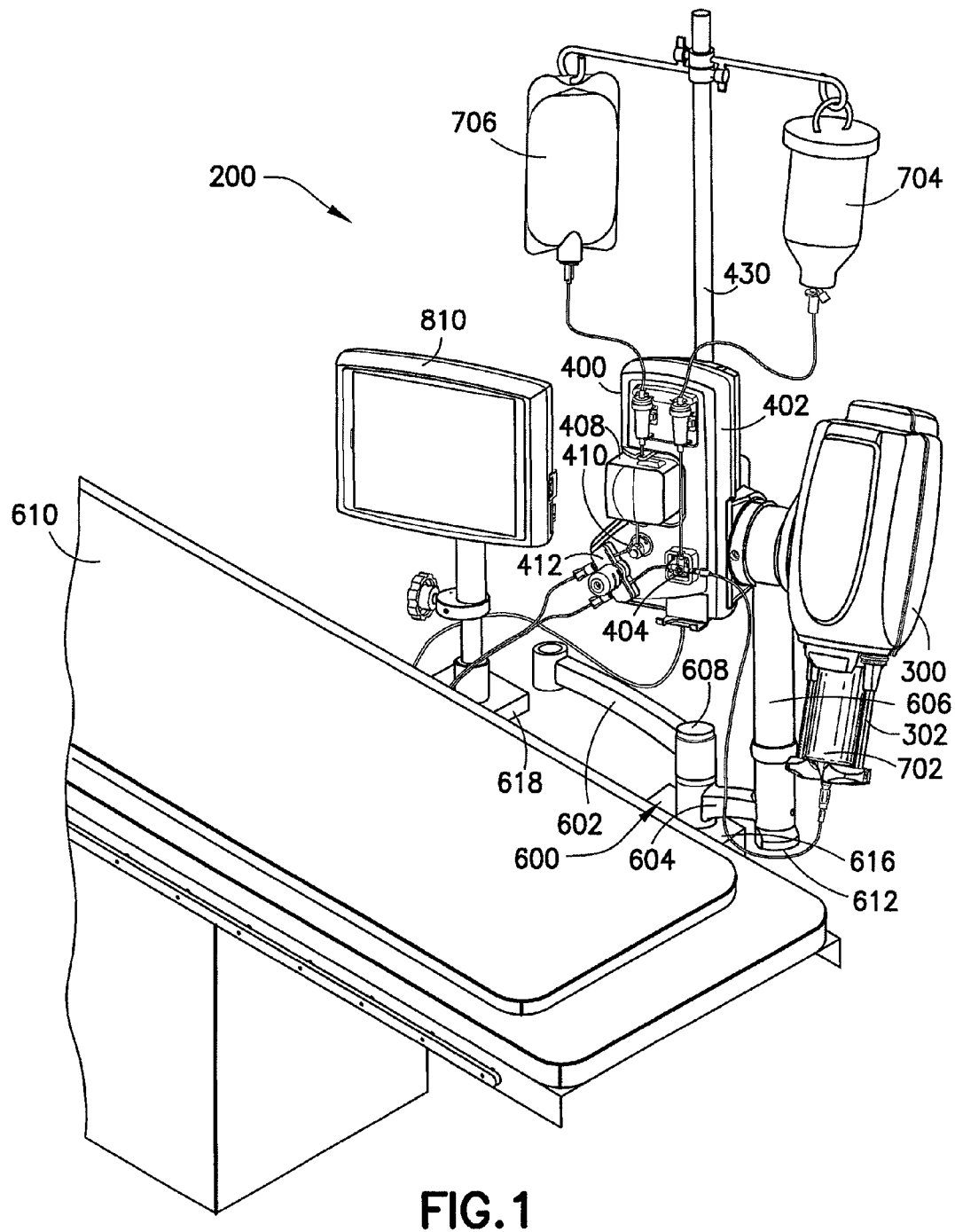
FIG. 1 is a perspective view of a fluid delivery system suitable for the intravenous infusion of fluids during diagnostic and therapeutic medical procedures, such as contrast-enhanced radiographic imaging.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices illustrated in the accompanying drawing figures and described herein are simply exemplary and should not be considered as limiting.

In the following description, systems and methods are disclosed for capacitance volume correction in fluid delivery systems that contain or include fluid-delivery bodies and associated pathways and other fluid delivery components used to convey fluids to a patient undergoing a medical procedure. In most instances, the systems and methods described herein have application in therapeutic and diagnostic medical procedures involving the intravenous infusion of fluids such as contrast-enhanced radiographic imaging. The systems and methods set forth herein automatically correct for capacitance volume effects when the fluid delivery components forming the fluid delivery path to the patient are under pressure. Such fluid delivery path components typically include fluid-containing "volumetric" bodies, such as syringes or drip chambers, and associated pathways, such as medical tubing, as well as other bodies or tubing connectors which may also be present in the fluid delivery path. Other examples of components which may be present in the fluid delivery path include valves such as stopcocks and pressure isolation valves. Typically, the foregoing examples of fluid delivery path components are made of polymeric materials that are at least partially-expandable or resiliently-expandable under pressure and, hence, expand or swell during operation of the fluid delivery system. Such expansion or swelling of fluid delivery path components can lead to inaccuracy in the delivery of fluid volumes to the patient.

In medical procedures, such as in the intravenous infusion of a contrast medium for contrast-enhanced radiographic imaging, it is often desirable to introduce a "sharp bolus" of fluid in which the medication and/or diagnostic fluid is introduced at increased pressure for rapid delivery into a specific location within the body. In the case of contrast-enhanced radiographic imaging, sufficient contrast media must be present at the specific location or region of interest in the body for diagnostic viable images to be taken during the procedure. Therefore, accuracy in the amount or volume of contrast media delivered to the patient is important. Moreover, as noted previously, it is desirable for the contrast media to be delivered as a "sharp bolus" of contrast media to the patient. Such a "sharp bolus" of contrast media in practice may be defined as a distinct or defined column of liquid having well-defined opposing ends or boundaries. Accordingly, accuracy in the amount of fluid delivered intravenously to a patient is often of importance in medical therapeutic and diagnostic procedures and such accuracy can be diminished by capacitance volume expansion of the fluid delivery path components when the fluid delivery system is under pressure. The systems and methods described herein employ techniques which may be expressed as an algorithm to correct for capacitance volume effects in fluid delivery bodies and other pathway components associated with fluid delivery systems to provide for the accurate delivery of fluids, such as medication and diagnostic fluids, in medical therapeutic and diagnostic procedures.

Figure 2:
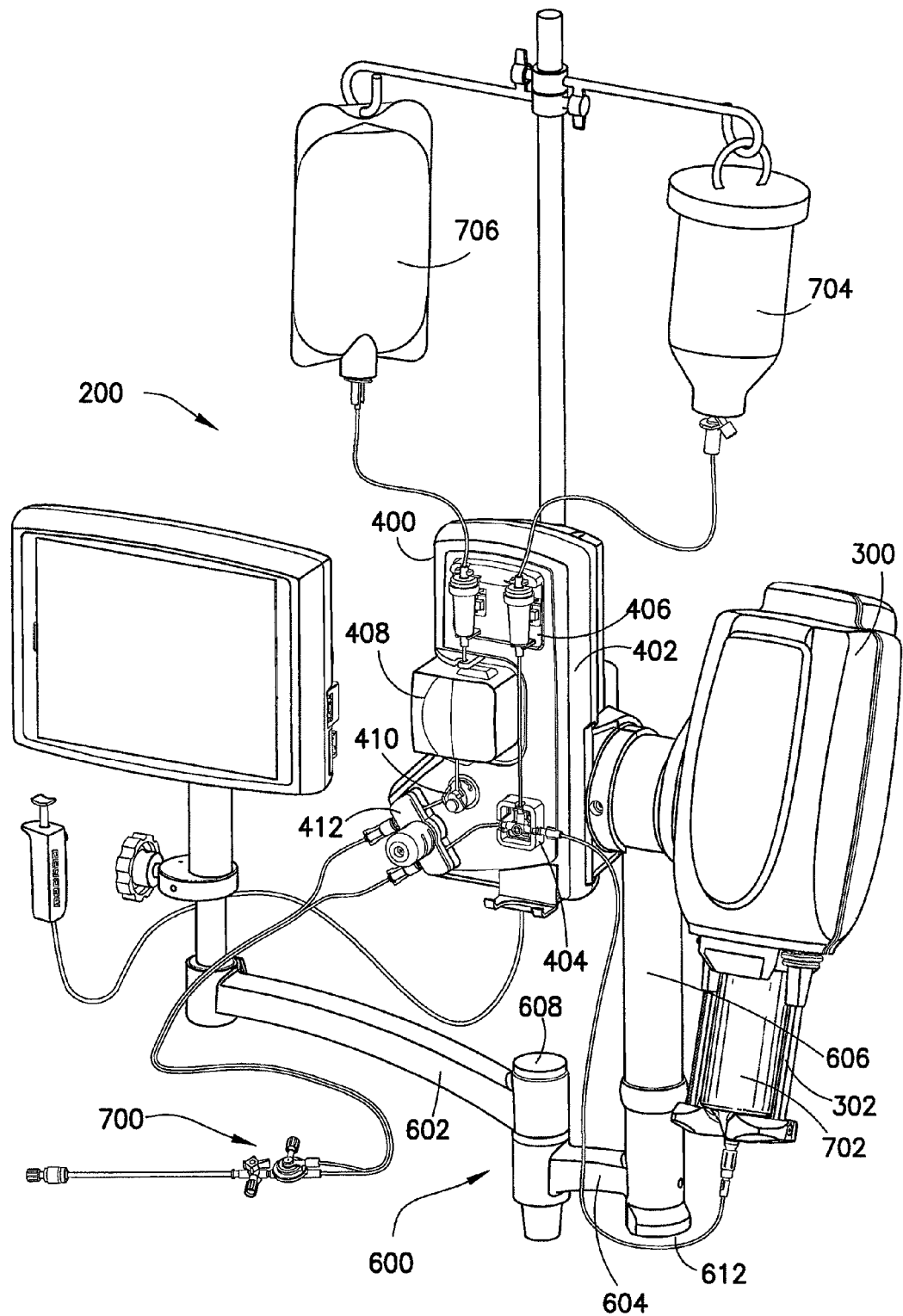
FIG. 2 is an enlarged perspective view of the fluid delivery system of FIG. 1 showing fluid handling components of the system.

The description hereinafter makes reference to a fluid delivery system provided for the delivery of contrast media and a diluent to a patient for contrast-enhanced radiographic imaging procedures for the purpose of explaining various aspects, features, and embodiments of the invention. However, this explanation should not be read as limiting the principles described herein to the delivery of contrast and a diluent to a patient for contrast-enhanced radiographic imaging procedures as the principles described herein are applicable to any situation where it is desired to deliver medical fluids in accurate quantities to a patient undergoing a therapeutic and/or diagnostic procedure. For the purposes of illustration and explanation, a fluid delivery system 200 that delivers contrast media and a diluent such as saline to a patient undergoing a diagnostic, contrast-enhanced radiographic imaging procedure is shown in FIGS. 1-2. The various components and elements as well as operation of fluid delivery system 200 is disclosed, for example, in U.S. patent application Ser. No. 11/551,027, filed Oct. 19, 2006, and published as United States Patent Application Publication No. 2007/0161970, and in U.S. patent application Ser. No. 11/825,866, filed Apr. 16, 2004, and published as United States Patent Application Publication No. 2005/0234407, the disclosures of which is incorporated fully herein by reference.

In United States Patent Application Publication No. 2005/0234407, for example, fluid injector or delivery system 200 generally includes a fluid injector 300 that is operatively associated with a fluid control module 400. The details of fluid injector 300 are set forth in U.S. patent application Ser. No. 10/818,477, filed Apr. 5, 2004, and published as United States Patent Application Publication No. 2004/0254533, the disclosure of which is incorporated fully herein by reference. Fluid injector 300 is adapted to support and actuate a syringe and the fluid control module 400 is associated with fluid injector 300 for controlling fluid flows delivered by fluid injector 300. Fluid delivery system 200 further includes a support assembly 600 adapted to support fluid injector 300 and fluid control module 400. Support assembly 600 may be configured as a movable platform or base so that the fluid delivery system 200 is generally transportable, or for connection to a standard hospital bed or examination table on which a patient will be located during a fluid delivery procedure. Fluid control module 400 is generally adapted to support and control a fluid delivery path or set 700 used to connect a syringe associated with fluid injector 300 to a catheter (not shown) to be associated with a patient. Additionally, fluid delivery system 200 typically further includes a user-input control section or device 810 for interfacing with computer hardware/software (e.g., electronic memory) of fluid control module 400 and/or fluid injector 300.

Support assembly 600 of the fluid delivery system 200 includes a support arm 602 for supporting control section 810, typically a user display and interface. A second support arm 604 extends from a support column 606 which generally supports fluid injector 300 and fluid control module 400. Support arms 602, 604 are associated with a rail interface 608 which is generally adapted to attach fluid delivery system 200 to a hospital bed or examination table 610. Support column 606 may include a pedestal interface 612 for attaching fluid delivery system 200 to a movable pedestal. Fluid delivery system 200 may either be attached to examination table 610 or movable pedestal as desired in utilizing fluid delivery system 200 for delivering contrast media and a diluent to a patient. When the fluid delivery system 200 is mounted to examination table 610, a rail mount 616 is attached to a rail 618 of the examination table 610. This allows rail interface 608 to be removably attached to the rail mount 616. Thus, rail mount 616 indirectly supports user display 810, injector 300, and fluid control module 400.

As indicated, fluid control module 400 is generally adapted to support and control fluid path 700 used to connect a syringe associated with fluid injector 300 to a catheter (not shown). Referring now to FIGS. 1-9, components of fluid path 700 are shown in greater detail. Fluid path 700 may be considered to include a syringe 702 that is to be associated with fluid injector 300. Fluid path 700 is generally used to associate syringe 702 with a first or primary source of injection fluid 704, also referred to herein as a primary fluid container, which will be loaded into syringe 702 for an injection procedure. Primary fluid container 704 may be contrast media in the case of a radiographic imaging procedure, as an example. Fluid path 700 is further adapted to associate a secondary or additional source of fluid 706, also referred to herein as a secondary fluid container, to be supplied or delivered to the patient via the catheter under the control of fluid control module 400. In a typical radiographic imaging procedure, such as angiography, saline is typically used as a secondary or flushing fluid which is supplied to the patient between injections of contrast media.

In a general injection procedure involving fluid delivery system 200, fluid injector 300 is filled with fluid from primary fluid container 704 and delivers the fluid via fluid path 700 to the catheter and, ultimately, the patient. Fluid control module 400 generally controls or manages the delivery of the injection through a valve associated with fluid path 700 which is controlled or actuated by a valve actuator on fluid control module 400. Fluid control module 400 is further adapted to deliver the fluid from secondary fluid container 706 under pressure via a peristaltic or a similar pump device on the fluid control module 400. Further specifics associated with fluid control module 400 are provided herein.

Fluid path 700 generally comprises a first section or set 710 and a second section or set 720. First section 710 is generally adapted to connect syringe 702 to primary fluid container 704 and to connect second section 720 to secondary fluid container 706. First section 710 is preferably a multi-patient section or set disposed after a preset number of injection procedures are accomplished with fluid delivery system 200. Thus, first section 710 may be used for a preset number of injection procedures involving one or more with patients and may then be discarded. First section 710 is preferably provided as a sterile set, in a sterile package. Second section 720 is a per-patient section or set which is preferably disposed of after each injection procedure involving fluid delivery system 200. In fluid path 700, first section 710 and second section 720 are placed in fluid communication by one or more connectors 708, the details of which are set forth in Publication No. 2005/0234407.

First section 710 includes a multi-position valve 712, a three-position stopcock valve, for example, which is adapted to be automatically controlled or actuated by a valve actuator on the fluid control module 400. Multi-position valve 712 is adapted to selectively isolate syringe 702, primary fluid container 704, and second section 720 to selectively allow fluid injector 300 to fill syringe 702 with fluid from primary fluid container 704, deliver fluid loaded into syringe 702 to second section 720, or isolate syringe 702 from primary fluid container 704 and second section 720. Multi-position valve 712 is connected to syringe 702 by a luer connection 714 which may be a standard luer connection known in the medical field. First section 710 further includes intervening drip chambers 716 associated with primary fluid container 704 and secondary fluid container 706. Drip chambers 716 may be replaced by priming bulbs in fluid path 700 as described in Publication No. 2005/0234407. Drip chambers 716 are adapted to be associated with primary and secondary fluid containers 704, 706 with conventional spike members 717. A fluid level sensing mechanism on fluid control module 400 is used to sense fluid levels in drip chambers 716 when fluid path set 700 is associated with fluid injector 300 and fluid control module 400. Generally, operation of fluid delivery system 200 includes filling, loading, or "priming" syringe 702 with fluid from primary fluid container 704 which passes to syringe 702 via drip chamber 716 associated with primary fluid container 704. Similarly, during operation of fluid delivery system 200, fluid, such as saline, from secondary fluid container 706 is supplied to second section 720 via drip chamber 716 associated with secondary fluid container 706. Drip chambers 716 are generally adapted to permit fluid level sensors associated with the level sensing mechanism on fluid control module 400 to detect the level of fluid in the drip chambers 716 by using optical or ultrasonic methods, for example.

Respective output lines 718 made, for example, of conventional low pressure medical tubing, are associated with the drip chambers 716 for connecting the drip chambers 716 to multi-position valve 712 and second section 720. The outlet of the multi-position valve 712 is connected to an output line 719 which is used to connect the multi-position valve 712 and syringe 702 to second section 720. Due to the high injection pressures which may be generated by fluid injector 300 during an injection procedure, output line 719 is preferably provided as high pressure medical tubing. An inlet to multi-position valve 712 is connected via an inlet line 721 to syringe 702, and is preferably provided as high pressure medical tubing.

Second section 720 generally includes a pressure isolation mechanism or valve 722, the details of which are described in Publication No. 2005/0234407. Pressure isolation mechanism 722 is connected by respective input lines 724, 726 and connectors 708 to first section 710. First input line 724 is preferably formed of conventional medical tubing and connects pressure isolation mechanism 722 with the drip chamber 716 associated with secondary fluid container 706. Second input line 726 is preferably formed of high pressure medical tubing and connects pressure isolation mechanism 722 with output line 719 connected to multi-position valve 712 and, ultimately, syringe 702 and primary fluid container 704. The tubing used for second input line 726 is preferably high pressure medical tubing.

A patient output line 728 is associated with pressure isolation mechanism 722 for connecting pressure isolation mechanism 722 with the catheter (not shown). A second multi-position valve 730, for example, in the form of a stopcock valve, may be provided in output line 728, as a shut-off feature. Multi-position valve 730 may be provided as a simple shut-off valve to isolate the catheter from first section 710 of fluid path 700. Patient output line 728 may further include a catheter connection 732 for associating fluid path 700 with the catheter.

Figure 7A:
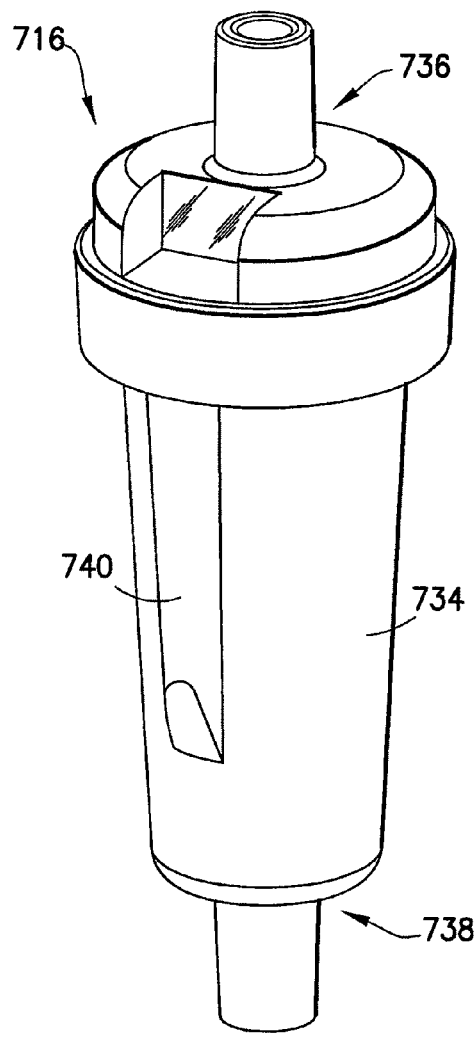
FIGS. 7A-7B are perspective views of embodiments of a drip chamber which may be used in the fluid path set of FIG. 3.
Figure 7B:
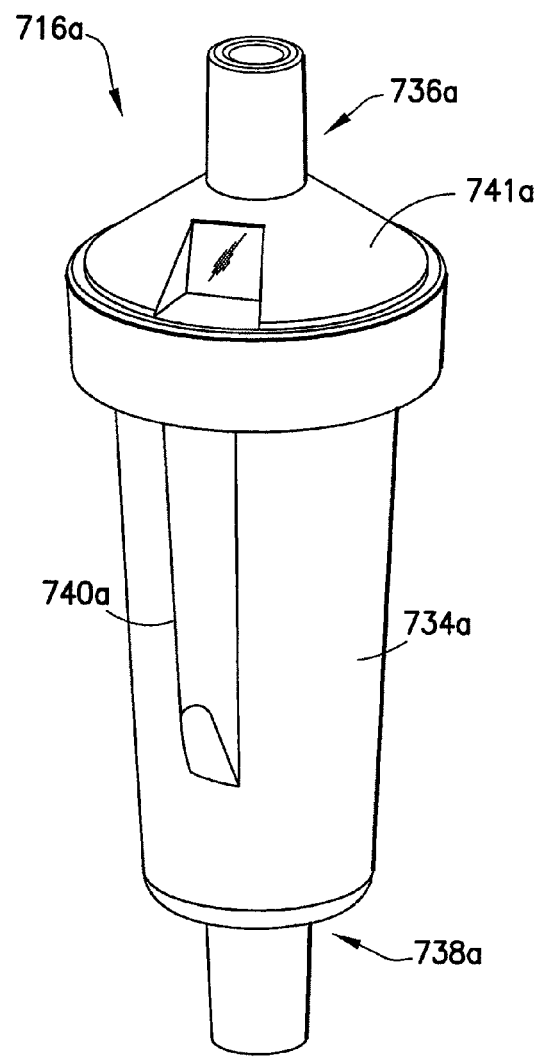
Figure 8:
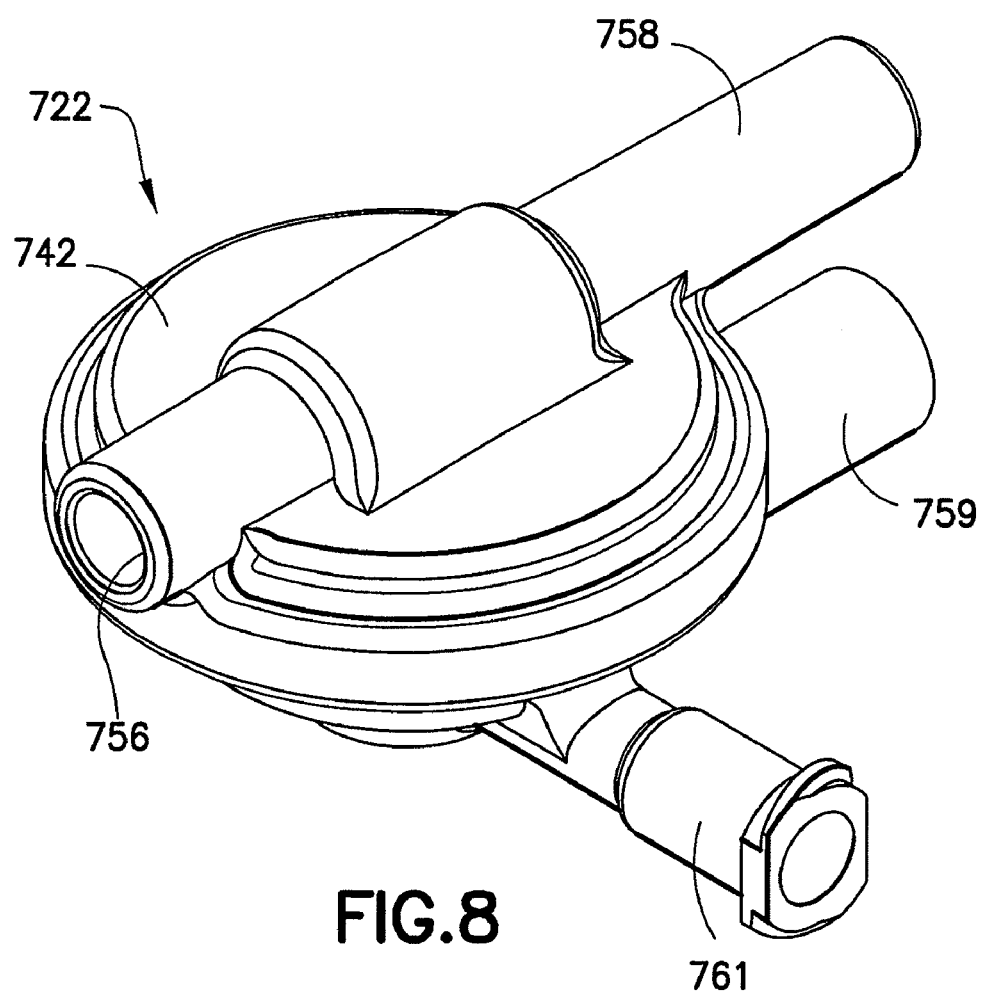
FIG. 8 is a perspective view of a pressure isolation valve which may be part of the fluid path set of FIG. 3.
Figure 9:
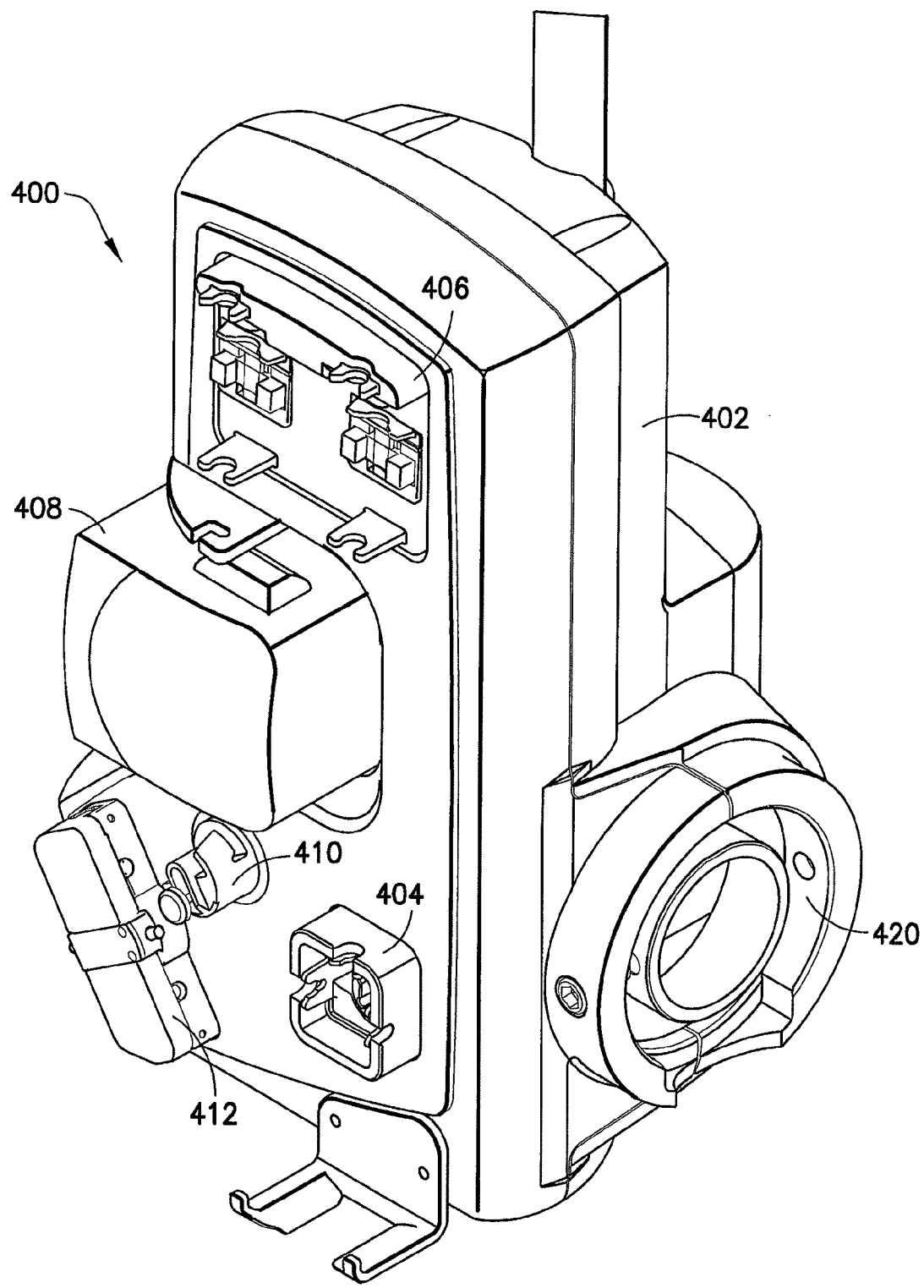
FIG. 9 is a perspective view of a fluid control module forming part of the fluid delivery system of FIGS. 1-2.

Referring to FIG. 7A, one of the drip chambers 716 used in fluid path 700 is shown in enlarged detail. Drip chamber 716 has an elongated body 734 with a top end 736 and a bottom end 738. Drip chamber body 734 is formed with a projection 740 which generally extends longitudinally along body 734 or in any desired configuration on body 734. Projection 740 is generally provided to interact with the fluid level sensing mechanism on fluid control module 400 and may be referred to as a "back" window because projection 740 will generally face the fluid level sensors in the fluid level sensing mechanism on fluid control module 400 when drip chamber 716 is associated with the fluid control module 400. FIG. 7B illustrates an alternative drip chamber 716a which has a tapered or domed upper end 741a which limits the accumulation of air bubbles in drip chamber 716a and, further, facilitates easy expulsion of air bubbles during priming of the drip chamber 716a during operational set-up of fluid path set 700.

Figure 3:
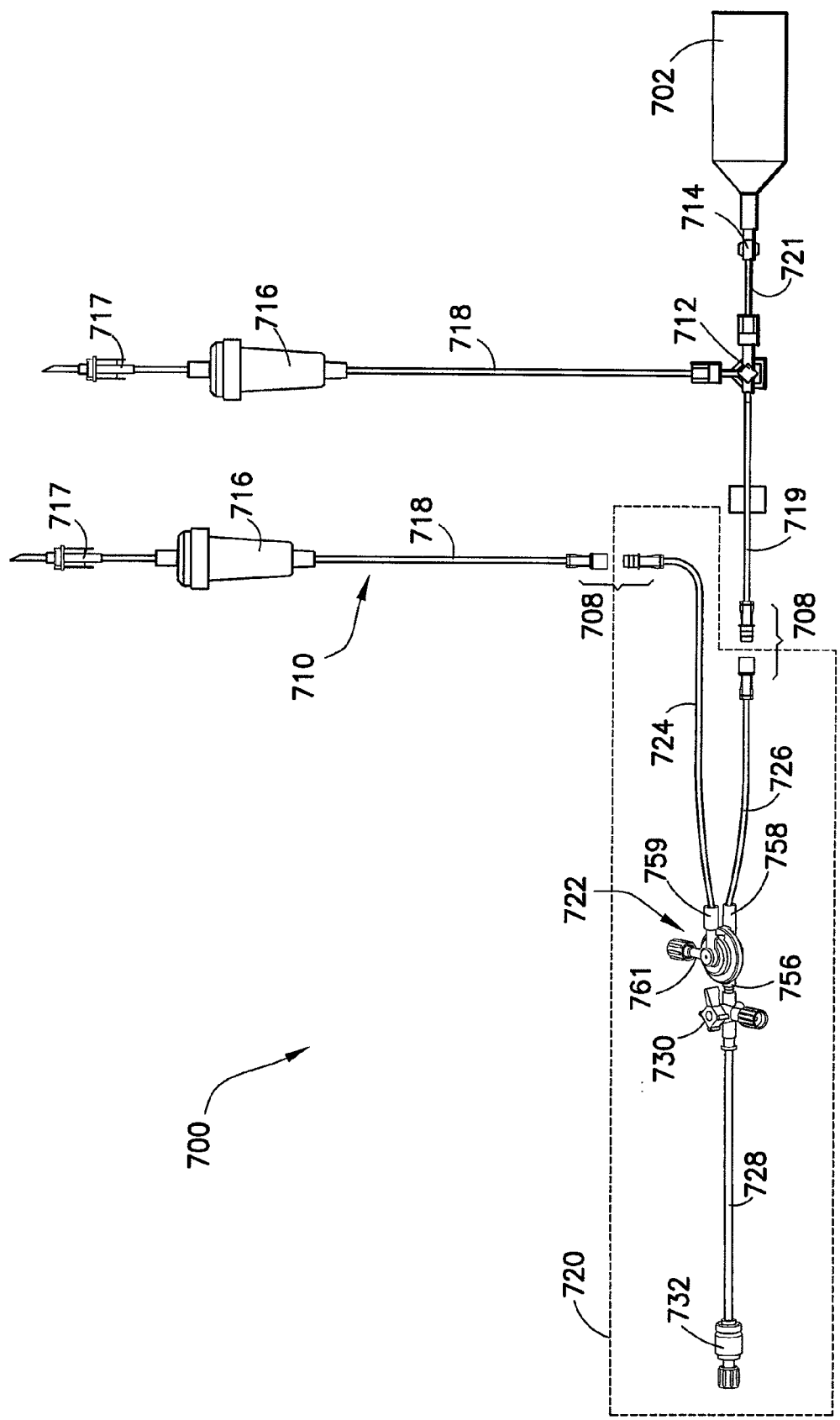
FIG. 3 is a side and partially perspective view of a fluid path set used in the fluid delivery system of FIGS. 1-2.
Figures 4A, 4B:
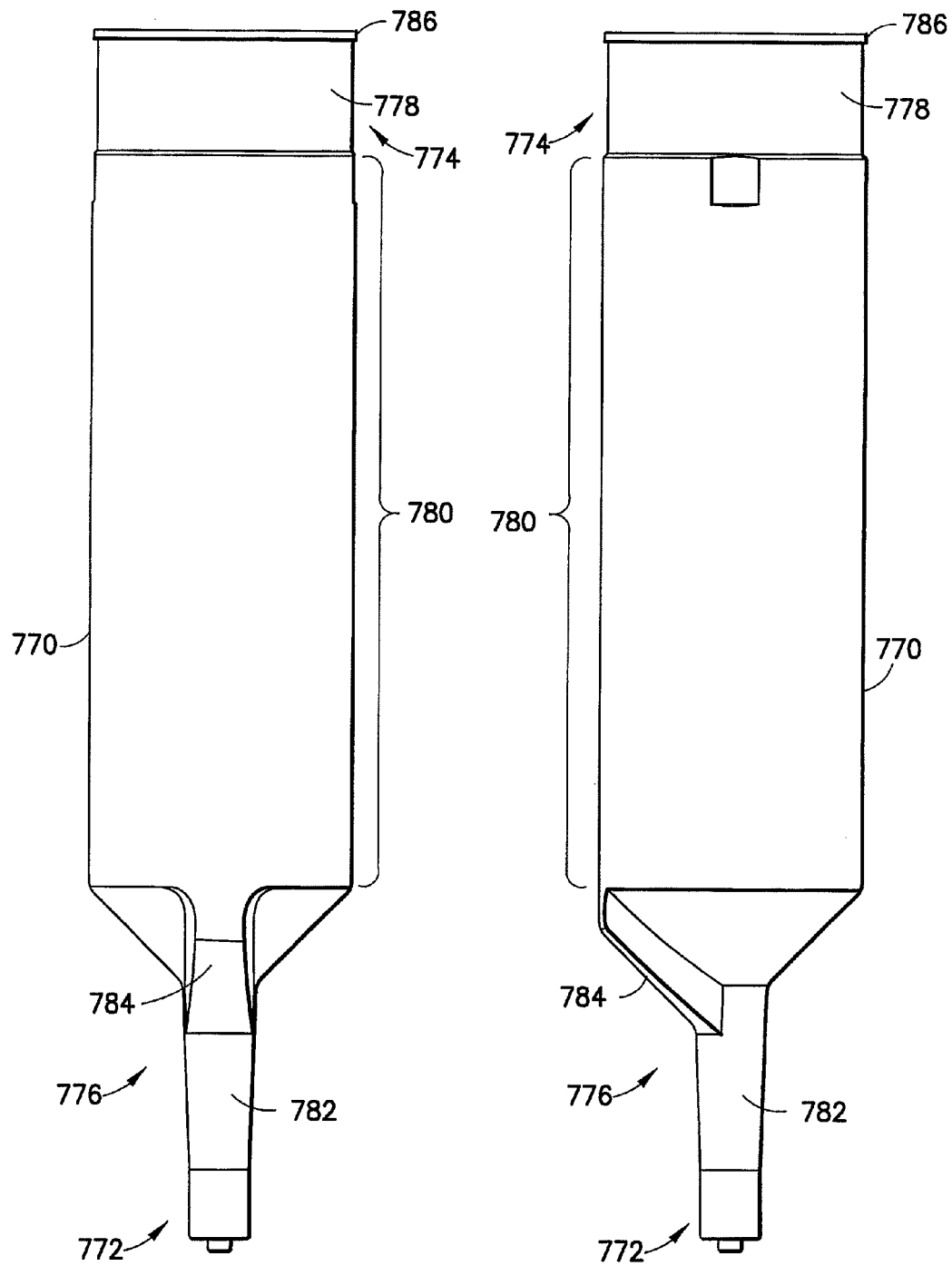
FIGS. 4A-4B are respective top and side views of a syringe used in the fluid delivery system of FIGS. 1-2 and which is part of the fluid path set of FIG. 3.
Figure 5:
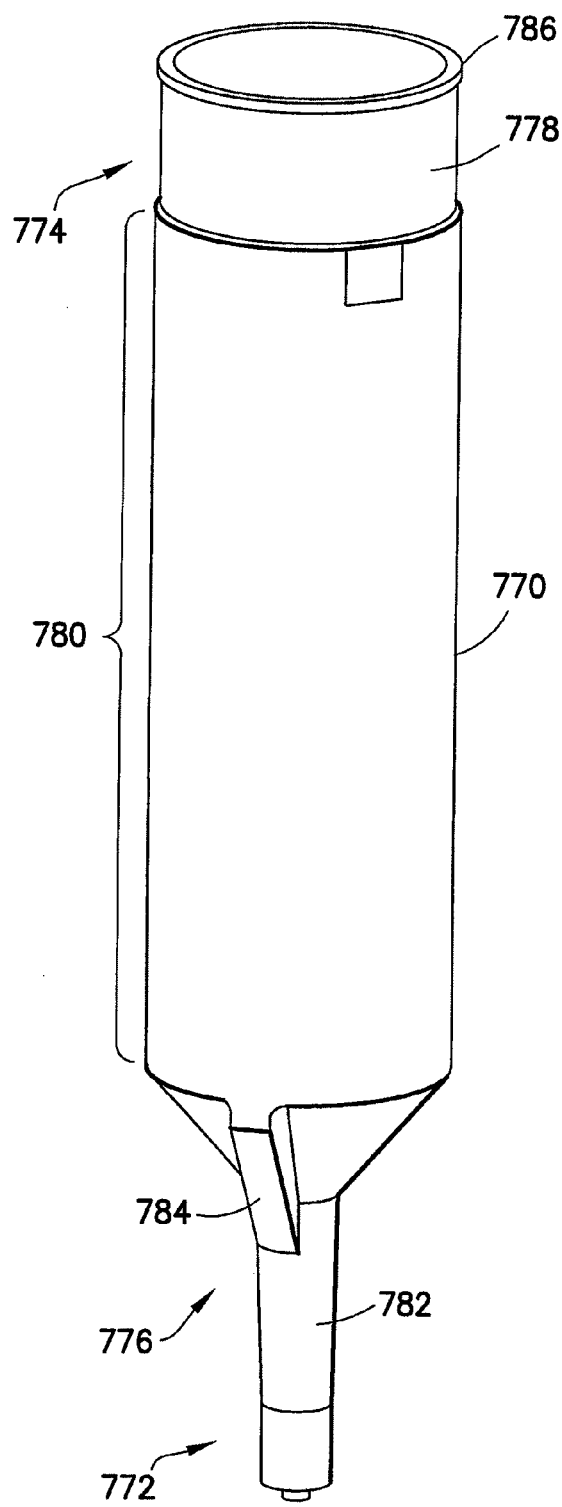
FIG. 5 is a perspective view of the syringe shown in FIGS. 4A-4B and used in the fluid delivery system of FIGS. 1-2 and which is part of the fluid path set of FIG. 3.

As will be appreciated from FIG. 3, as an example, pressure isolation mechanism 722 operates as a merge point for contrast and saline for delivery to a patient during a fluid injection or delivery procedure, and comprises an outlet port 756 connected to multi-position valve 730, a high pressure port 758 associated with high pressure input line 726 and a low pressure port 759 associated with low pressure input line 724. One aspect of pressure isolation mechanism 722 relates to using a pressure transducer associated with a pressure isolation port 761 to take hemodynamic blood pressure signal readings and obtain other relevant information associated with the fluid delivery procedure involving the delivery of contrast and/or saline to a patient. Pressure isolation mechanism 722 provides automatic overpressure protection to this transducer during delivery of contrast at high pressure to the pressure isolation mechanism 722.

Syringe 702 associated with fluid path 700 comprises an elongated, cylindrical syringe body 770 having a front or distal end 772 and a rear or proximal end 774. Syringe body 770 has an injection section 776 formed at the distal end 772 and includes an expansion section 778 at the proximal end 774. A generally cylindrical center section or main body 780 of syringe body 770 connects injection section 776 and expansion section 778. Center section or main body 780 has a relatively uniform outer diameter. Injection section 776 tapers to form an elongated injection neck 782 which has a relatively small inner diameter compared to the inner diameter of center section 780. Injection section 776 and injection neck 782 generally form the discharge outlet of syringe 702. Injection neck 782 of injection section 776 includes a distal end structure 783 such as a luer-type connection structure which is adapted to connect via a suitable luer fitting to tubing, for example connected to a catheter used in an angiographic procedure. Suitable luer fittings for this purpose is disclosed in U.S. patent application Ser. No. 11/099,147, filed Apr. 5, 2005 (United States Patent Application Publication No. 2005/0171487), the disclosure of which is incorporated herein by reference in its entirety, and in U.S. patent application Ser. No. 11/004,670, filed Dec. 3, 2004, and U.S. patent application Ser. No. 11/426,348, filed Jun. 26, 2006, published as United States Publication No. 2007/0129705, the disclosures of which are incorporated herein by reference.

Syringe 702 is supported by a pressure jacket assembly 302 comprising a restraining, front load pressure jacket 302 associated with fluid injector 300. An alignment flange 784 is provided on syringe body 770 which is used as a device to align and load syringe 702 into the pressure jacket assembly 302 of fluid injector 300. The proximal end 774 of syringe body 770 further defines an outward extending lip 786 which is adapted to engage or contact an actuating device associated with the fluid injector 300 when syringe 702 is loaded into the accommodating pressure jacket assembly. The raised proximal lip 785 provides a sufficient, outward extending proximal structure at proximal end 774 of syringe 702 to enable syringe 702 to engage and depress or move the actuating device to register or cause a signal to be sent by the actuating device indicating that a syringe is loaded or associated with the fluid injector 300. Expansion section 778 is formed as part of syringe body 770 to provide a storage area or location for a syringe plunger 788 disposed in syringe body 770. Generally, a reduced wall thickness at the expansion section 778 of syringe body 770 accommodates the expansion and plastic creep of the plastic syringe body 770 which may occur after long periods of storage wherein syringe plunger 788 is seated or disposed in syringe body 770.

Figure 6A:
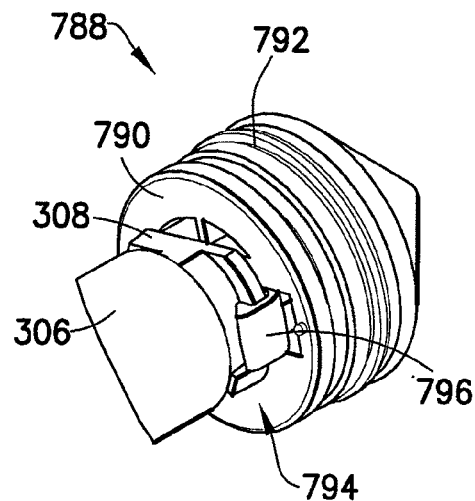
FIG. 6A is a perspective view showing coupling engagement between an injector drive piston of a fluid injector forming part of the fluid delivery system of FIGS. 1-2 and a syringe plunger disposed in the syringe of FIGS. 4-5.
Figure 6B:
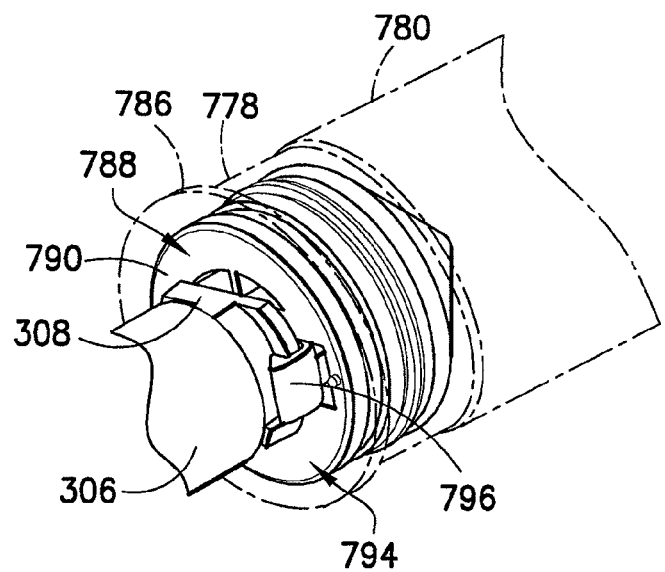
FIG. 6B is a perspective view similar to FIG. 6A and further showing the syringe of FIGS. 4-5 in phantom.

Referring, in particular, to FIGS. 6A-6B, when syringe 702 is inserted into the pressure jacket assembly 302 associated with fluid injector 300, syringe plunger 788 is engaged by an injector drive piston 306 and moved forward from expansion section 778 to the center section or main body 780 of syringe 702, which may be referred to as the "working zone" of syringe 702. The injector drive piston 306 is extendable through a faceplate F of fluid injector 300 for imparting motive forces to syringe plunger 788. Injector drive piston 306 is preferably motorized. The injector drive piston 306 includes a rectangular injector end plate 308 which is adapted to capture syringe plunger 788 and impart motion to syringe plunger 788 in syringe 702. Syringe plunger 788 is generally conical-shaped to cooperate with the conical portion of the injection section 776 of syringe body 770. Syringe plunger 788 includes a base member 790 that is substantially enclosed by a cover 792 which forms the general conical shape of the syringe plunger 788 and may be made of rubber, as an example. Syringe plunger 788 includes a coupling end 794 that faces the proximal end 774 of syringe body 770. In one embodiment, a pair of flexible lug or coupling members 796 extends outward from coupling end 794 for engaging injector drive piston 306 and, more particularly, injector end plate 308 attached to the injector drive piston 306, as described in U.S. Pat. Nos. 5,873,861 and 5,947,935, the disclosures of which are incorporated herein by reference. Coupling members 796 are flexible and may be integrally formed with base member 790. In an alternative embodiment, coupling members 796 may be substantially fixed or rigid, as described in U.S. Pat. No. 4,677,980, incorporated herein by reference.

Fluid control module 400 generally includes a housing 402, a valve actuator 404 for controlling multi-position valve 712, a fluid level sensing mechanism 406 for determining the presence or absence of fluid in drip chambers 716, a peristaltic pump 408, an optional automatic shut-off or pinch valve 410, and an air detector assembly 412. Housing 402 defines a side port 420 for associating fluid injector 300 with the fluid control module 400. Valve actuator 404 is adapted to support and actuate multi-position valve 712 associated with primary section 710 of fluid path set 700. Multi-position valve 712, as indicated previously, may be a three-position stopcock valve. Valve actuator 404 is generally adapted to selectively move or actuate multi-position valve 712 between three set positions or states, including: (1) an inject or open position, (2) a fill position, and (3) a closed or isolation position. In the inject position, syringe 702 of fluid path 700 is in fluid communication with the second section 720 of fluid path 700. In the fill position, syringe 702 is in fluid communication with primary fluid container 704 via the associated drip chamber 716. Finally, in the closed position, syringe 702 is isolated from primary fluid container 704 and the second section 720 of fluid path set 700. Generally, multi-position valve 712 is inserted into a valve retainer associated with valve actuator 404 to associate the multi-position valve 712 with the valve actuator 404.

Fluid level sensing mechanism 406 generally interfaces with the drip chambers 716 associated with the primary and secondary fluid containers 704, 706. Fluid level sensor 406 is provided to indicate to the operator of fluid delivery system 200 that sufficient injection fluid, either primary contrast media or secondary saline, is available for an injection or flushing procedure. Fluid level sensor 406 is generally adapted to warn the operator when the fluid level in drip chambers 716 is below a level sufficient to conduct an injection procedure. Fluid level sensor 406 is provided as a safety feature to ensure that air is not introduced into the fluid path 700 during an injection procedure or flushing procedure involving fluid delivery system 200.

Fluid control module 400 includes a peristaltic pump 408 that is associated with secondary fluid container 706. Peristaltic pump 408, or an equivalent device, is used to deliver fluid from secondary fluid container 706 to a patient typically between fluid injections from primary fluid container 704 which are delivered via syringe 702 and fluid injector 300. Peristaltic pump 408 is generally adapted to deliver a set flow rate of secondary fluid, for example saline, to the patient via second section 720 of fluid path 700.

Optional shut-off or pinch valve 410 of the fluid control module 400 is provided downstream of peristaltic pump 408 and is used as a back-up fluid shut-off mechanism to discontinue fluid flow to second section 720 of the fluid path 700 when peristaltic pump 408 ceases operation. Pinch valve 410 is adapted to open for fluid flow during operation of peristaltic pump 408 and automatically close when peristaltic pump 408 ceases operation to prevent air from being introduced into the second section 720 of fluid path set 700. Pinch valve 410 generally prevents gravity flow to the second section 720 of fluid path 700 when peristaltic pump 408 is not in operation.

Air detector assembly 412 associated with fluid control module 400 is adapted to detect gross air columns that may be present in output line 718 connected to the drip chamber 716 associated with secondary fluid container 706, and in output line 719 associated with multi-position valve 712. Air detector assembly 412 is generally adapted to initiate a signal to computer hardware/software associated with fluid control module 400 and/or fluid injector 300, if gross air is detected in the medical tubing forming output line 719 associated with multi-position valve 712 or in the medical tubing forming output line 718 and associated with peristaltic pump 408.

Figure 10:
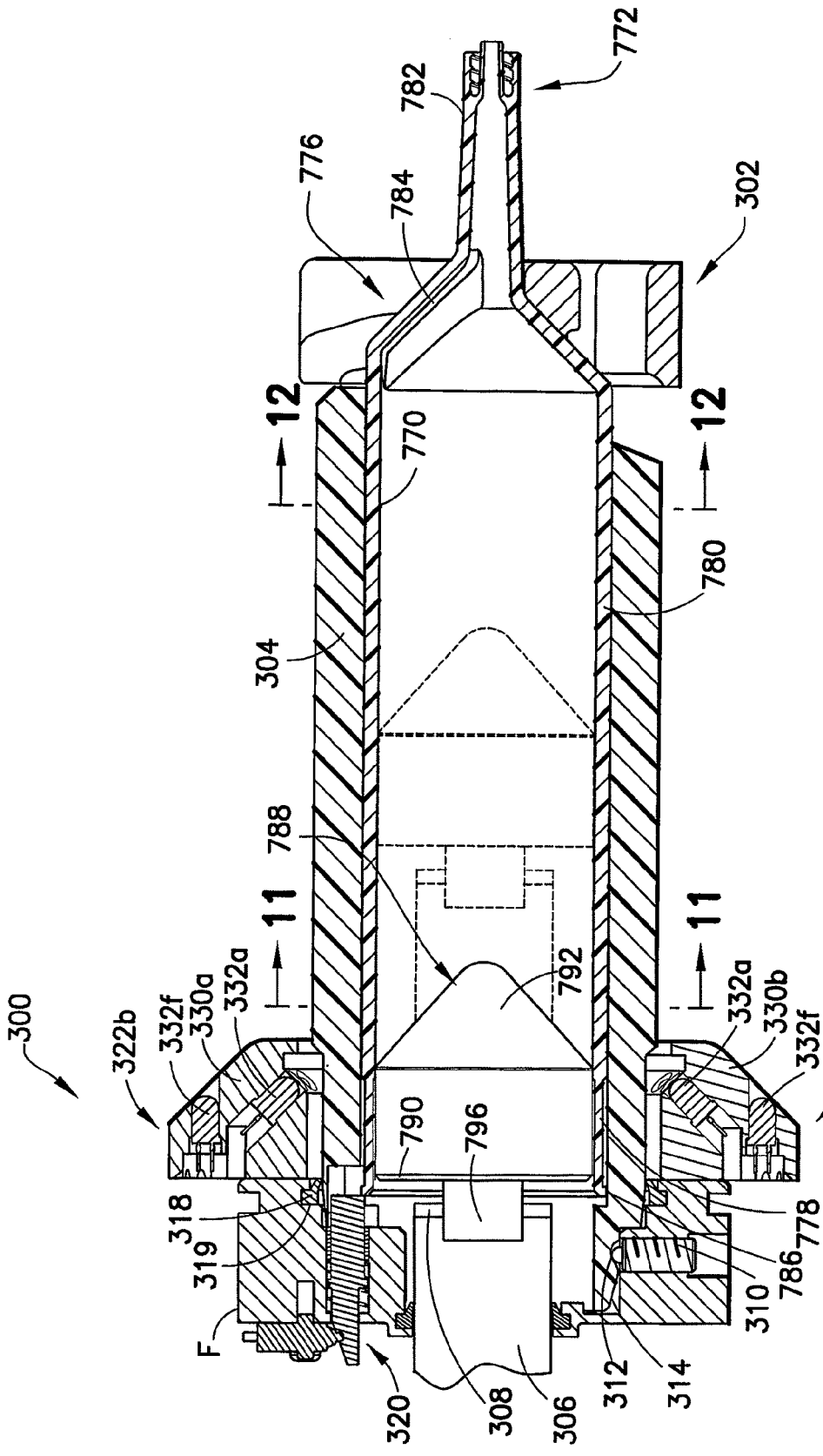
FIG. 10 is a cross-sectional view of a pressure jacket assembly of the fluid injector associated with the fluid delivery system of FIGS. 1-2, and further showing a syringe supported by the pressure jacket assembly.

In fluid injector 300, pressure jacket 304 of pressure jacket assembly 302 is adapted to engage or connect directly to faceplate F of fluid injector 300. This engagement or connection between pressure jacket 304 and faceplate F is secured by the engagement of, for example, a spring-biased engagement tab 310 provided in the faceplate F with a corresponding engagement recess 312 formed in the proximal end of pressure jacket 304. Engagement recess 312 is formed in an elongated proximal portion of pressure jacket 304, as illustrated in FIG. 10, and may be in the form of a groove in this elongated proximal portion of pressure jacket 304. An external cam surface 314 may be provided on the elongated proximal portion of pressure jacket 304 to facilitate depression of engagement tab 310 as the pressure jacket 304 is associated or engaged with faceplate F of fluid injector 300. As shown in detail in FIG. 10, a sealing bushing 318 may be provided in a circumferential recess or groove 319 formed in faceplate F. Sealing bushing 318 is generally adapted to engage the circumferential outer surface of pressure jacket 304 to form a barrier that substantially prevents contaminants and liquids from entering the opening in faceplate F through which injector drive piston 306 extends to engage syringe plunger 788 in syringe 702. A syringe sensor 320 may also be associated with faceplate F and is positioned such that when syringe 702 is loaded into pressure jacket 302, rear lip 786 on the proximal end 774 of syringe body 770 engages and actuates syringe sensor 320. Syringe sensor 320 is generally adapted to generate a signal indicating the presence of syringe 702 in pressure jacket 304 which may be transmitted to the control unit(s) associated with fluid injector 300 and/or fluid control module 400.

Another feature of pressure jacket assembly 302 relates a lighting arrangement provided for illuminating pressure jacket 304 and syringe 702 loaded therein. Pressure jacket assembly 302 includes a pair of opposing light sources 322a, 322b, which are located on opposite sides of pressure jacket 304. Opposing light sources 322a, 322b include respective light source housings 330a, 330b and internally positioned lights 332, such as light-emitting diodes (LED's) or similar light-emitting elements. Light source housings 330a, 330b are connected to faceplate F, for example, by any suitable mechanical or adhesive means. While the light source housings 330a, 330b are illustrated as being located on the top and bottom of faceplate F in FIG. 10, other configurations, such as locating light source housings 330a, 330b on opposing lateral sides of faceplate F are also possible. The respective light source housings 330a, 330b each typically include a plurality of lights 332, such as at least one inward-directed or angled light 332a to illuminate pressure jacket 304 and the syringe 702 loaded therein on opposing sides thereof, and at least one forward directed light 332f used for other purposes such as indicating when the fluid injector head 300 is ready to begin an injection procedure.

The foregoing description identifies the general components of fluid delivery system 200 with additional details of the fluid delivery system 200 and its operation being available from United States Publication Nos. 2005/0234407 and 2004/0254533. Briefly, however, it is noted that during operation of fluid delivery system 200 in order deliver fluid to a patient, multi-position valve 712 is rotated to the "inject" position identified previously which places syringe 702 in fluid communication with second section 720 of fluid path 700. In this inject position, syringe 702 has been pre-loaded with injection fluid, typically from primary fluid container 704 and fluid path 700 has been purged of air. Once fluid injector 300 is actuated, injector drive piston 306 moves forward, having been previously coupled with syringe plunger 788 in syringe 702. As injector drive piston 306 moves forward, syringe plunger 788 moves forward in syringe body 770 from the "storage" expansion section 778 and into the main body 780 or working zone of syringe 702. If desired, a handcontroller may be provided and associated with fluid injector 300 or fluid control module 400 to operate fluid injector 300. As the injector drive piston 306 moves forward within syringe 702, the fluid therein, typically contrast media, is delivered under pressure to fluid path 700 and, in particular, second section 720 of fluid path 700 for delivery to the patient intravenously via use of an indwelling catheter. When a desired amount of contrast media has been delivered as determined by a preset protocol programmed into the control device(s) associated with fluid injector 300 and/or fluid control module 400 or by an operator ceasing actuation of a handcontroller or like device, multi-position valve 712 is operated to a closed or "off" position. However, multi-position valve 712 may remain open for a preset or predetermined amount of time to allow residual contrast media to exit syringe 702 and for contrast volume correction purposes as described hereinafter.

Fluid delivery system 200 operates to create a sharp bolus of injection fluid within fluid path 700 for delivery to the patient. A sharp bolus of contrast media may be defined as a distinct or defined column of liquid having well-defined opposing ends or boundaries. The creation of a sharp bolus of injection fluid due to operation of multi-position valve 712 concurrently results in system pressure buildup upstream of the multi-position valve 712. To remove this excess pressure, injector drive piston 306 may be moved slowly backward or proximally in a controlled manner to relieve system pressure but so not to create a vacuum condition in fluid path 700 as described hereinafter.

Figure 11:
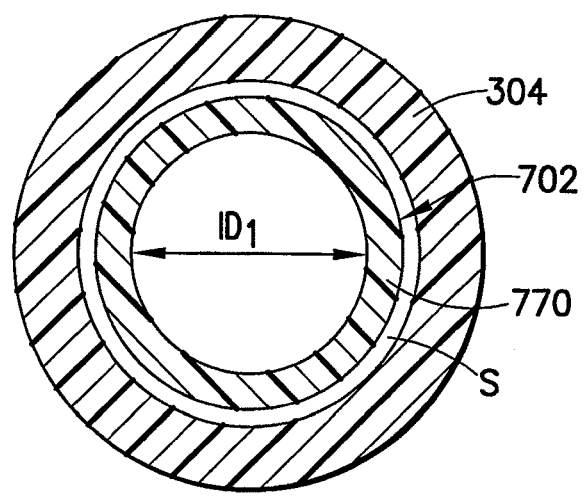
FIG. 11 is a cross-sectional view taken along lines 11-11 in FIG. 10.
Figure 12:
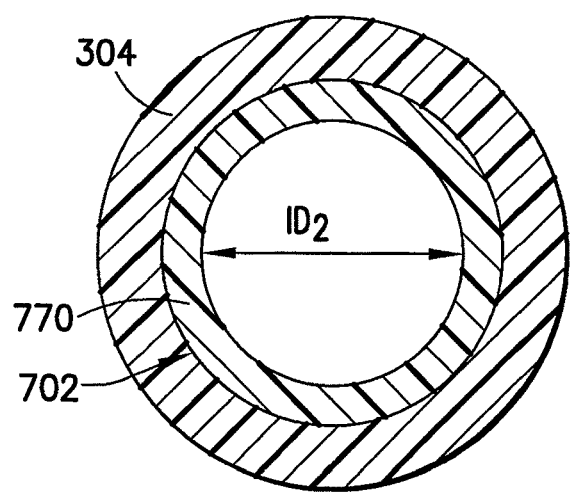
FIG. 12 is a cross-sectional view taken along lines 12-12 in FIG. 10.

In order to produce the foregoing described "sharp bolus" effect, multi-position valve 712 is ideally operated to the closed or isolation position shortly (milliseconds) after injector drive piston 306 ceases forward movement. However, truncating fluid flow in this manner creates substantial volume delivery errors due to fluid capacitance effects. This fluid capacitance effect is generally illustrated in FIGS. 11-12. In FIG. 11, syringe 702 is unpressurized and, as a result, in an unswollen state. This is schematically illustrated in cross-sectional form in FIG. 11, wherein spacing or clearance is present between the outer circumference of syringe body 770 and the inner circumference of pressure jacket 304. Syringe body 770 has an inside diameter $ID_1$ in the unpressurized state. As injector drive piston 306 engages syringe plunger 788 and moves the syringe plunger 788 forward in syringe body 770 to expel injection fluid, pressure increases in syringe body 778 and injection fluid is ejected under pressure from syringe 702 into fluid path 700. However, as syringe plunger 788 moves distally, syringe body 770 swells outward as shown schematically in FIG. 12 wherein this outward expansion is restrained by the presence of pressure jacket 304. This swelling or outward expansion results in an expansion in volume of syringe body 770 and an under-delivery of fluid to the patient upon closure of multi-position valve 712. This expansion or swelling is known as capacitance volume and is a retained volume of injection fluid that does not enter fluid path 700 and, hence, is not delivered to the patient.

Figure 13:
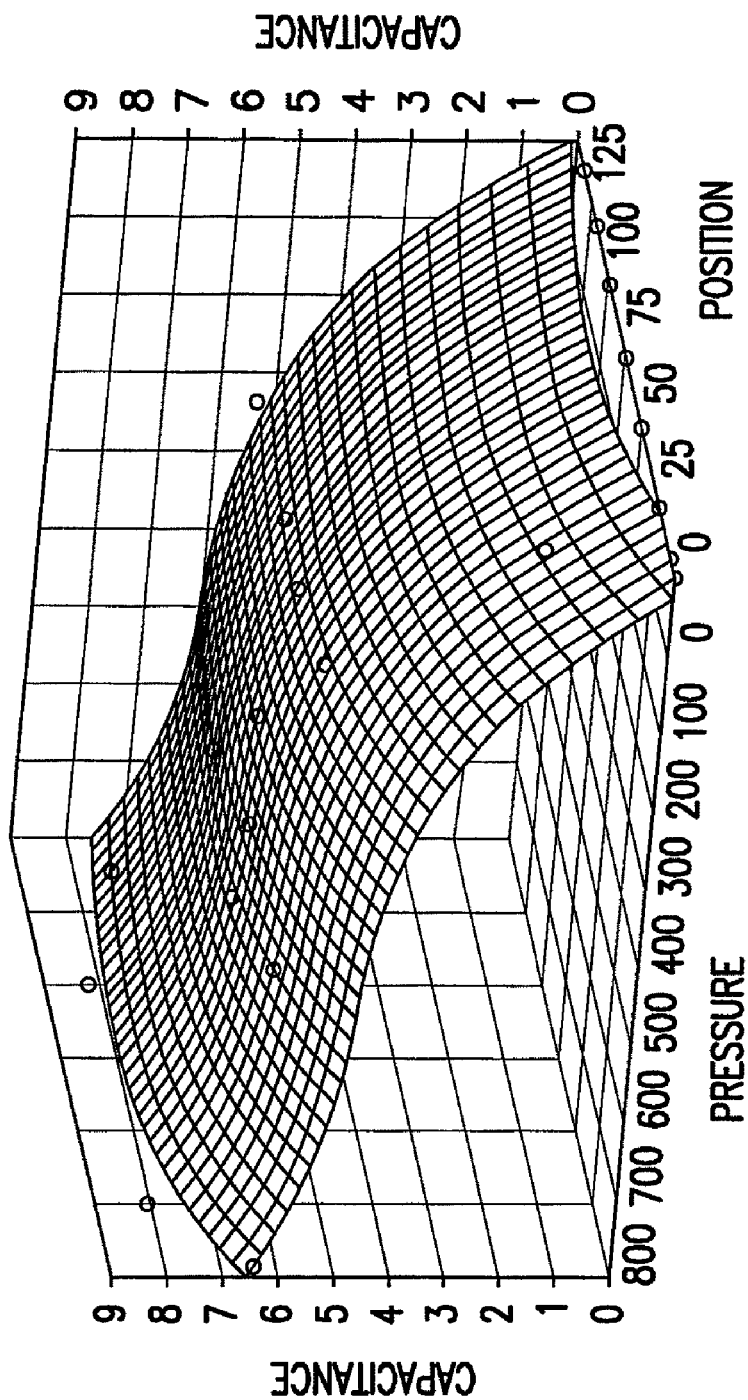
FIG. 13 is a three-dimensional surface plot of capacitance volume correction in accordance with aspects of the invention.

In order to account for under-delivery of fluid to the patient, a method is needed to allow the injector drive piston 306 and, hence, syringe plunger 788 to over-travel by a predicted capacitance volume, and then retract to relieve the swell and depressurize the system. The inventors have discovered that the required capacitance volume correction factor is dominated primarily by system pressure and axial position of syringe plunger 788 within syringe 702. From this discovery, methodology was developed that selectively augments or controls the operation of injector drive piston 306 based on system pressure and the position of the syringe plunger 788 in syringe 702. Testing using fluid delivery system 200 results in testing data displayed in FIG. 13 as a three-dimensional surface plot representation of the test data collected. FIG. 13 confirms the inventors' conclusion that the required compensating capacitance volume increases with system pressure and decreases with the nearness of syringe plunger 788 to the injection section 776 of the syringe body 770 of syringe 702.

The three-dimensional surface plot function displayed in FIG. 13 which governs over-travel behavior of injector drive piston 306 is given in the following equation:

$$\text{Over Travel (ml)} = C_1 + C_2*x + C_3*x^{-2} + C_4*x^{-3} + C_5*y + C_6*y^{-2} + C_7*y^{-3}$$

(Where: $C_1 = -0.811$; $C_2 = 0.039$; $C_3 = -0.00035$; $C_4 = 9.05\text{E}-7$; $C_5 = 0.0269$; $C_6 = -4.43\text{e}-5$; $C_7 = 2.607\text{e}-8$; x axis=pressure; y axis=position)

This relation characterizes system fluid capacitance or "swell" and the subsequent compensating capacitance volume required as a function of system pressure and position of syringe plunger 788 within syringe 702. This relation accounts primarily for "swell" in syringe 702 which is the primary contributing factor to fluid volume under-delivery as the "swell" associated with other components of fluid path 700 under pressure are negligible as in the case of tubing 719, or there is substantially no "swell" as in the case of pressure isolation valve 722 which is typically formed of hard plastic materials.

As noted in the foregoing, fluid delivery system 200 may be operated to create a "sharp bolus" effect by operating multi-position valve 712 to the closed or isolation position shortly (milliseconds) after injector drive piston 306 ceases forward movement which minimizes the decay of fluid flow and providing a "sharp bolus" profile. As further noted in the foregoing, the process of truncating fluid flow in this manner has the effect of suppressing a portion of the fluid that would typically be delivered to fluid path 700 and, in particular, second section 720 of fluid path 700 from syringe 702. This volume of suppressed fluid, typically defined as the capacitance volume, is captured in the swell of the components of fluid path 700 including syringe 702 and can be substantial (on the order of 5-9 ml). This capacitance volume is based on a number of factors, but is quantifiable. Capacitance volume can greatly impact the accuracy of fluid delivery to the patient in fluid delivery system 200. Moreover, as noted in the foregoing, the suppressed or capacitance volume is dictated by the pressures achieved in the system and by the location of syringe plunger 788 within syringe 702. The act of storing this capacitance volume, by default, keeps the fluid delivery system 200 under pressure which is not desirable and is potentially hazardous to an operator.

The over-travel strategy introduced previously corrects for capacitance volume to achieve accurate delivery of injection fluid amounts or volumes to a patient while maintaining a sharp bolus injection profile. Over-travel of the injector drive piston 306 is then coupled with a rapid back drive of the injector drive piston 306, for example, on the order of 25 milliliters of volume to relieve or reduce system pressure and orient the injector drive piston 306 in a position commanded by the control device(s) associated with fluid injector 300 and/or fluid control module 400 or system operator via a handcontroller. In other words, this pull-back repositions injector drive piston 306 back to the originally desired or intended stop position after closure of multi-position valve 712. A specific Example of the implementation of the foregoing methodology now follows.

EXAMPLE

An empirical model of fluid delivery system 200 employing a syringe made of PET and analogous to syringe 702 was used to determine required over-travel of injector drive piston 306 needed to achieve volume accuracy of ±1.5%+1 ml. Static testing was first performed for pressures of 300, 600, and 900 psi and ending volumes of 125, 100, 75, 50, 30, and 10 ml. This testing entailed pressurizing syringe 702 while recording required displacement of syringe plunger 788 needed to achieve the aforementioned pressures. This relative displacement comprises the amount of capacitance volume believed to be indicative of truncated volume if multi-position valve 712 were closed at the end of movement of injector drive piston 306. The empirically derived relative displacement is then added as the value for over-travel to effectively deliver the required capacitance volume, also referred to previously as under-delivered fluid. Additionally, this value also comprises the value of retraction of injector drive piston 306 to return the injector drive piston 306 to its correct (non-capacitance) linear travel position. Follow-on dynamic testing utilized the over-travel information developed in static testing.

As stated previously, static testing of fluid delivery system 200 was initially conducted to find the relationship between over travel as a function of axial position of syringe plunger 788 and system pressure. The data obtained by static testing was intended to provide effective starting values for capacitance volume correction and was further believed to be able to provide desirable accuracies when fluid delivery system 200 achieved steady state pressure. Additional adjustments were anticipated as being required to compensate for dynamic behavior after determining a "static" response of the system. Table I herein provides the capacitance volume (ml) characterization as a function of pressure and axial location of syringe plunger 788 in syringe 702. It is noted that the data in Table I was taken for a syringe with ID=1.606 and pressure jacket ID=1.8345, OD=2.5692.

TABLE I

Characterization of Static Capacitance Volumes

| Ending Volume (ml) | Injected Volume (ml) | Pressure (psi) | Capacitance Volume (ml) |
|---|---|---|---|
| 140 | 10 | 300 | 7.17 |
| 140 | 10 | 600 | 8.73 |
| 140 | 10 | 900 | 10.23 |
| 120 | 30 | 300 | 6.68 |
| 120 | 30 | 600 | 7.64 |
| 120 | 30 | 900 | 9.09 |
| 100 | 50 | 300 | 5.71 |
| 100 | 50 | 600 | 7.80 |
| 100 | 50 | 900 | 9.00 |
| 75 | 75 | 300 | 4.82 |
| 75 | 75 | 600 | 5.71 |
| 75 | 75 | 900 | 6.97 |
| 50 | 100 | 300 | 4.02 |
| 50 | 100 | 600 | 5.31 |
| 50 | 100 | 900 | 6.84 |
| 25 | 125 | 300 | 3.72 |
| 25 | 125 | 600 | 4.98 |
| 25 | 125 | 900 | 6.54 |
| 10 | 140 | 300 | 3.78 |
| 10 | 140 | 600 | 5.11 |
| 10 | 140 | 900 | 6.44 |
| 5 | 145 | 300 | 3.62 |
| 5 | 145 | 600 | 5.05 |
| 5 | 145 | 900 | 6.41 |

Figure 14:
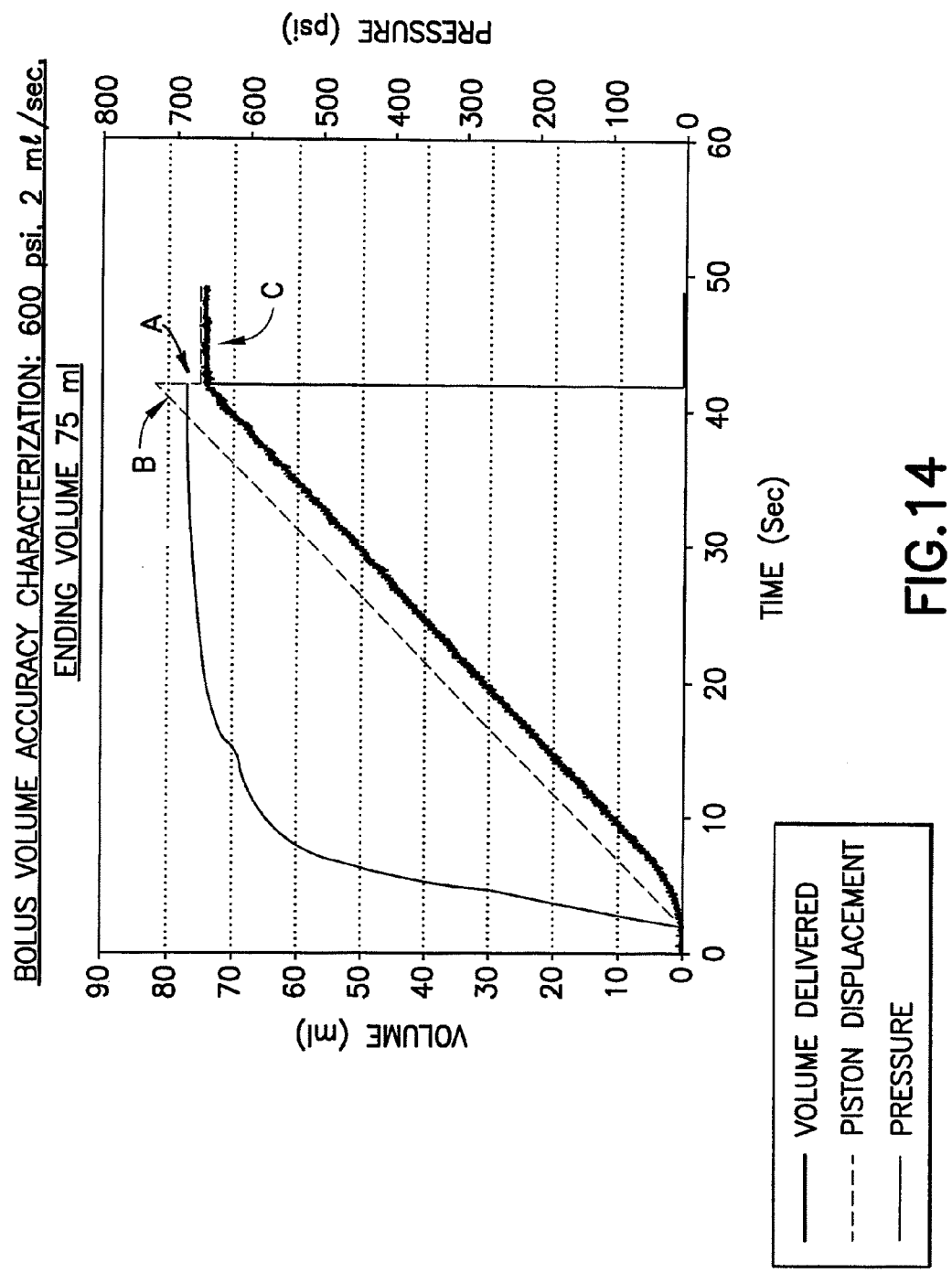
FIG. 14 is a graph illustrating exemplary capacitance volume accuracy results at steady-state conditions for given flow and pressure conditions in the fluid delivery system.

Once the static values were obtained in Table I, the dynamic system testing was accomplished for dynamic capacitance volume correction factors based on syringe pressure, volume delivered, and piston travel information. FIG. 14 illustrates a typical plot of the data recorded in static and dynamic testing. From this plot, as the volume is delivered, system pressure approaches steady state. The injector drive piston 306 then over-travels by a designated amount. For this particular data set, total displacement of injector drive piston 306 is 75 ml (a programmed volume) plus 5.71 ml (over-travel volume—"A") for a total of 80.71 ml. Fluid delivery system 200 then delays at 200 ms ("B") and retracts back to the 75 ml mark. As system 200 quickly depressurizes and the actual volume delivered converges on the programmed volume, and stops at this value, a sharp bolus behavior ("C") or response is induced.

Figure 15:
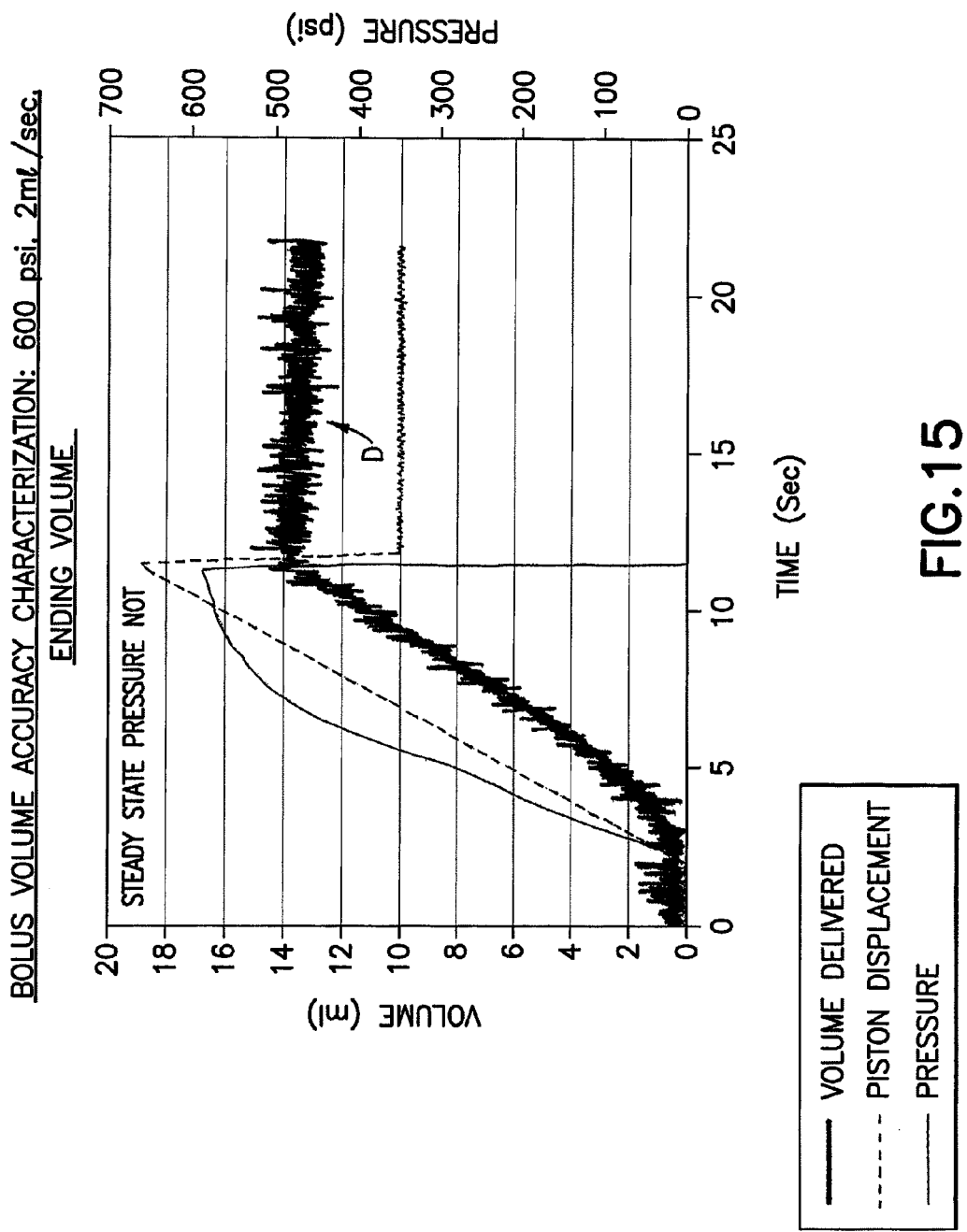
FIG. 15 is a graph illustrating exemplary capacitance volume accuracy results at non-steady-state conditions for given flow and pressure conditions in the fluid delivery system.

The data obtained in static and dynamic testing of system 200 showed steady state pressures were achieved for higher volume deliveries, but still had a ramping effect at lower volumes. Subsequently, since system 200 did not achieve full steady state pressure, the system 200 has not completely expanded, thus the correction factors can be over compensated. This will induce a small vacuum in syringe 702. This result is illustrated at "D" in FIG. 15 for volume delivery of 10 ml.

It is noted that a sharp bolus profile was achieved in all testing phases. Accuracy percentages with a positive sign (+) in Table II below represent the situation where the capacitance volume compensation factor was greater than required and would entail a slight vacuum in syringe 702 upon completion. Accuracy percentages with a negative sign (−) in Table II below represent the situation where under compensation occurred and, thus, slight residual pressure in syringe 702 remains. Table II, which follows, illustrates these results:

TABLE II

Achieved Volume Accuracies

| Rate (ml/s) | Max Pressure Achieved (psi) | Ending Volume Target (ml) | Volume Delivered (ml) | Volume Accuracy (%) |
| --- | --- | --- | --- | --- |
| 2 | 314 | 140 | 11.65 | 16.52 |
| 2 | 586 | 140 | 13.88 | 38.80 |
| 2 | 900 | 140 | 12.96 | 26.60 |
| 2 | 319 | 120 | 31.25 | 4.15 |
| 2 | 671 | 120 | 31.40 | 4.67 |
| 2 | 929 | 120 | 31.39 | 4.63 |
| 2 | 319 | 100 | 50.21 | 0.42 |
| 2 | 678 | 100 | 51.51 | 3.03 |
| 2 | 942 | 100 | 50.75 | 1.50 |
| 2 | 318 | 75 | 73.97 | −1.37 |
| 2 | 686 | 75 | 74.70 | −0.40 |
| 2 | 934 | 75 | 73.56 | −1.92 |
| 2 | 325 | 50 | 98.69 | −1.31 |
| 2 | 742 | 50 | 98.69 | −1.31 |
| 2 | 992 | 50 | 99.16 | −0.84 |
| 2 | 327 | 25 | 124.12 | −0.70 |
| 2 | 618 | 25 | 123.79 | −0.97 |
| 2 | 945 | 25 | 123.48 | −1.22 |
| 10 | 283 | 140 | 14.25 | 42.50 |
| 10 | 615 | 75 | 75.76 | 1.01 |
| 10 | 871 | 75 | 75.96 | 1.28 |

Utilizing the data from Tables I and II above, finalized capacitance volume correction factors were obtained and are provided in Table III below; based on the finalized capacitance volume correction factors the surface plot shown in FIG. 13 was generated to provide estimations across a range of system operating pressures and axial position of syringe plunger 788 in syringe 702:

TABLE III

Augmented Correction Factors

| Syringe Position (ml) | Injected Volume (ml) | Pressure (psi) | Original Capacitance (ml) | Correction Factor | New Capacitance (ml) |
| --- | --- | --- | --- | --- | --- |
| 140 | 10 | 300 | 7.171 | −1.65 | 5.521 |
| 140 | 10 | 600 | 8.732 | −3.65 | 5.082 |
| 140 | 10 | 900 | 10.226 | −2.96 | 7.266 |
| 120 | 30 | 300 | 6.675 | −1.25 | 5.425 |
| 120 | 30 | 600 | 7.636 | −1.16 | 6.476 |
| 120 | 30 | 900 | 9.097 | −1.39 | 7.707 |
| 100 | 50 | 300 | 4.71 | −0.21 | 5.5 |
| 100 | 50 | 600 | 7.802 | −1.51 | 6.292 |
| 100 | 50 | 900 | 8.997 | −0.75 | 8.247 |
| 75 | 75 | 300 | 4.482 | 1.03 | 5.512 |
| 75 | 75 | 600 | 5.71 | 0.3 | 6.01 |
| 75 | 75 | 900 | 6.962 | 1.44 | 8.412 |
| 50 | 100 | 300 | 4.017 | 1.31 | 5.327 |
| 50 | 100 | 600 | 5.312 | 1.31 | 6.622 |
| 50 | 100 | 900 | 6.839 | 0.84 | 7.679 |
| 25 | 125 | 300 | 3.718 | 0.88 | 4.598 |
| 25 | 125 | 600 | 4.98 | 1.21 | 6.19 |
| 25 | 125 | 900 | 6.541 | 1.52 | 8.061 |

The foregoing methodology which resulted in the surface plot in FIG. 13 and accompanying equation utilized to calculate required capacitance volume correction factors needed for sharp bolus operation of system 200 may be implemented as an algorithm by which to control movement of injector drive piston 306 and, further, operation of multi-position valve 712. Such an algorithm may be part of the programming associated with the control devices associated with fluid injector 300 and/or fluid control module 400 or an external control device (e.g., separate controller) used to operate fluid injector 300 and/or fluid control device 400. In summary, the foregoing methodology controls operation of injector drive piston 306 to over-travel a prescribed or sufficient volume amount/distance based on pressure in the system and axial position of the syringe plunger 788 in syringe 702 to compensate for capacitance volume effects in the components of fluid path 700, primarily resulting from "swell" of syringe body 770 during operation of system 200. Once the required over-travel has been effected, multi-position valve 712 is operated to a closed position and the injector drive piston 306 may be retracted sufficiently to relieve system residual pressure.

While several fluid delivery systems embodiments were disclosed in the foregoing description employing techniques to correct for capacitance volume effects in fluid-delivery bodies and associated fluid pathways used in the fluid delivery systems system, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A method of capacitance volume correction in a fluid delivery system comprising a fluid-delivery expandable body comprising:
   pressurizing the expandable body by reducing a volume in the expandable body with movement of a pressurizing element;
   determining an over-travel distance for the pressurizing element; and ceasing pressurization by stopping movement of the pressurizing element after allowing the pressurizing element to over-travel the over-travel distance to compensate for expansion of the expandable body under pressure.

2. A method as claimed in claim 1, further comprising controlling movement of the pressurizing element with an algorithm.

3. A method as claimed in claim 1, further comprising abruptly isolating the expandable body from a downstream process after the pressurizing element over-travels the over-travel distance.

4. A method as claimed in claim 3, wherein the step of abruptly isolating the expandable body comprises closing an isolation valve.

5. A method as claimed in claim 4, further comprising retracting the pressurizing element within the expandable body to relieve pressure within the expandable body.

6. A method as claimed in claim 5, further comprising opening the isolation valve to place the expandable body in fluid communication with a source of fluid for the expandable body.

7. A method as claimed in claim 6, further comprising refilling the expandable body with fluid from the source of fluid by retracting the pressurizing element within the expandable body.

8. A method of capacitance volume correction in a syringe comprising a plunger and filled with an injection fluid comprising:
    pressurizing the syringe by reducing a volume in a syringe body with movement of the plunger;
    determining an over-travel distance for the plunger; and
    stopping movement of the plunger after allowing the plunger to over-travel the over-travel distance to compensate for expansion of the syringe body under pressure.

9. A method as claimed in claim 8, further comprising abruptly isolating the syringe from a downstream process after the plunger over-travels the over-travel distance.

10. A method as claimed in claim 9, wherein the step of abruptly isolating the syringe comprises closing an isolation valve.

11. A method as claimed in claim 10, further comprising retracting the plunger within the syringe to relieve pressure within the syringe body.

12. A method as claimed in claim 11, further comprising opening the isolation valve to place the syringe in fluid communication with a source of injection fluid for the syringe.

13. A method as claimed in claim 12, further comprising refilling the syringe by retracting the plunger within the syringe.

14. A method of controlling delivery of fluid to a downstream process comprising:
    providing a fluid-containing expandable body in fluid communication with the downstream process, the expandable body comprising a pressurizing element;
    pressurizing the expandable body by moving the pressurizing element forward in the expandable body to reduce a volume therein;
    determining an over-travel distance for the pressurizing element; and
    ceasing movement of the pressurizing element after allowing the pressurizing element to over-travel the over-travel distance to compensate for expansion of the expandable body under pressure.

15. A method as claimed in claim 14, wherein the expandable body comprises a syringe and the pressurizing element comprises a plunger disposed in the syringe.

16. A method as claimed in claim 14, further comprising abruptly isolating the expandable body from the downstream process after the pressurizing element over-travels the over-travel distance.

17. A method as claimed in claim 16, wherein the step of abruptly isolating the expandable body comprises closing an isolation valve.

18. A method as claimed in claim 17, further comprising retracting the pressurizing element within the expandable body to relieve pressure within the expandable body.

19. A method as claimed in claim 18, further comprising opening the isolation valve to place the expandable body in fluid communication with a source of fluid for the expandable body.

20. A method as claimed in claim 19, further comprising refilling the expandable body with fluid from the source of fluid by retracting the pressurizing element within the expandable body.

* * * * *